(12) United States Patent
Shimazu et al.

(10) Patent No.: US 12,192,611 B2
(45) Date of Patent: Jan. 7, 2025

(54) INFORMATION PROCESSING DEVICE, VISUAL LINE DETECTION SYSTEM, VISUAL LINE DETECTION METHOD, AND VISUAL LINE DETECTION PROGRAM

(71) Applicant: SONY INTERACTIVE ENTERTAINMENT INC., Tokyo (JP)

(72) Inventors: Takashi Shimazu, Tokyo (JP); Shinichi Hirata, Tokyo (JP); Makoto Koizumi, Tokyo (JP); Hiromasa Naganuma, Tokyo (JP)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 226 days.

(21) Appl. No.: 17/630,496

(22) PCT Filed: Aug. 7, 2020

(86) PCT No.: PCT/JP2020/030312
§ 371 (c)(1),
(2) Date: Jan. 26, 2022

(87) PCT Pub. No.: WO2021/029342
PCT Pub. Date: Feb. 18, 2021

(65) Prior Publication Data
US 2022/0272256 A1    Aug. 25, 2022

(30) Foreign Application Priority Data
Aug. 14, 2019  (JP) .................................. 2019-148854

(51) Int. Cl.
*H04N 23/611*    (2023.01)
*G06T 7/20*    (2017.01)
(Continued)

(52) U.S. Cl.
CPC ............. *H04N 23/611* (2023.01); *G06T 7/20* (2013.01); *G06T 7/70* (2017.01); *G06V 40/18* (2022.01);
(Continued)

(58) Field of Classification Search
None
See application file for complete search history.

(56) References Cited

U.S. PATENT DOCUMENTS 8,971,570 B1 * 3/2015 Raffle .................. G02B 27/017
382/103
10,108,261 B1 * 10/2018 Hall ........................ G06V 40/19
(Continued)

FOREIGN PATENT DOCUMENTS

JP    11-56782 A    3/1999
JP    2011-125693 A    6/2011
(Continued)

OTHER PUBLICATIONS

Notice of Reasons for Refusal dated Feb. 7, 2023, from Japanese Patent Application No. 2019-148854, 3 sheets.
(Continued)

*Primary Examiner* — Stefan Gadomski
(74) *Attorney, Agent, or Firm* — XSENSUS LLP

(57) ABSTRACT

Provided is an information processing device including a light source control section that changes intensity of light of a light source which irradiates eyes of a user, a reception section that receives, from an event driven vision sensor including a sensor which generates an event signal when detecting a change in intensity of a light to be incident thereon, the event signal indicating a position and a time of the change in intensity of the light reflected by the eyes of the user, and a visual line detection section that identifies the light source corresponding to the event signal on the basis of
(Continued)

a relative positional relation among the eyes of the user, the light source, and the vision sensor, and of the event signal generated at the same time that control is carried out by the light source control section, to detect a visual line of the user.

10 Claims, 6 Drawing Sheets

(51) Int. Cl.
*G06T 7/70* (2017.01)
*G06V 40/18* (2022.01)
*H04N 23/56* (2023.01)

(52) U.S. Cl.
CPC ... *H04N 23/56* (2023.01); *G06T 2207/30201* (2013.01)

(56) References Cited

U.S. PATENT DOCUMENTS

| | | | | |
|---|---|---|---|---|
| 10,466,779 | B1* | 11/2019 | Liu | G02B 27/0093 |
| 10,984,236 | B2* | 4/2021 | St-Hilaire | G06F 3/013 |
| 11,064,387 | B1* | 7/2021 | Movshovich | H04N 13/194 |
| 11,435,820 | B1* | 9/2022 | Hirsh | G06F 3/0346 |
| 2014/0192092 | A1* | 7/2014 | Aruga | G02B 27/017 |
| | | | | 345/690 |
| 2015/0085250 | A1* | 3/2015 | Larsen | A61B 3/113 |
| | | | | 351/206 |
| 2016/0310060 | A1* | 10/2016 | Li | A61B 3/14 |
| 2016/0334869 | A1* | 11/2016 | Zhang | G06F 3/013 |
| 2017/0205876 | A1* | 7/2017 | Vidal | G01S 17/87 |
| 2018/0303333 | A1* | 10/2018 | Takeda | A61B 3/117 |
| 2019/0095164 | A1* | 3/2019 | Yamaura | G10L 15/26 |
| 2019/0158819 | A1* | 5/2019 | Hong | G06F 3/01 |
| 2019/0244429 | A1* | 8/2019 | Flaherty-Woods | G06T 19/006 |
| 2019/0258062 | A1* | 8/2019 | Aleem | G02B 27/0172 |
| 2019/0259279 | A1* | 8/2019 | Narumi | G06V 40/19 |
| 2019/0317597 | A1* | 10/2019 | Aleem | G06V 40/19 |
| 2019/0317598 | A1* | 10/2019 | Aleem | H04N 13/383 |
| 2019/0324532 | A1* | 10/2019 | Aleem | G06F 3/012 |
| 2020/0000391 | A1* | 1/2020 | Hato | G06F 3/011 |
| 2020/0278539 | A1* | 9/2020 | Petljanski | G02B 27/0179 |
| 2020/0348755 | A1* | 11/2020 | Gebauer | G06F 18/2413 |
| 2020/0372677 | A1* | 11/2020 | Yoon | G06V 40/193 |
| 2021/0197845 | A1* | 7/2021 | Mimura | B60W 60/005 |
| 2021/0240331 | A1* | 8/2021 | Olson | G06F 3/013 |

FOREIGN PATENT DOCUMENTS

| | | |
|---|---|---|
| JP | 2014-535098 T | 12/2014 |
| JP | 2018-085725 A | 5/2018 |
| JP | 2018-196730 A | 12/2018 |
| WO | 2019147677 A1 | 8/2019 |

OTHER PUBLICATIONS

International Search Report and Written Opinion mailed Sep. 29, 2020, from PCT/JP2020/030312, 8 sheets.

* cited by examiner

INFORMATION PROCESSING DEVICE, VISUAL LINE DETECTION SYSTEM, VISUAL LINE DETECTION METHOD, AND VISUAL LINE DETECTION PROGRAM

TECHNICAL FIELD

The present invention relates to an information processing device, a visual line detection system, a visual line detection method, and a visual line detection program.

BACKGROUND ART

There has been known an event driven vision sensor in which each pixel detects a change in intensity of light to be incident to generate a signal asynchronously in time. Such an event driven vision sensor is advantageous to be able to operate at low power and high speed, in comparison with a frame-based vision sensor that scans all pixels for predetermined cycles, specifically, an image sensor such as a CCD (Charge Coupled Device) or a CMOS (Complementary Metal Oxide Semiconductor).

A technique relating to such an event driven vision sensor is recited in PTL 1 and PTL 2, for example.

CITATION LIST

Patent Literature

[PTL 1]
JP 2014-535098T
[PTL 2]
JP 2018-085725A

SUMMARY

Technical Problem

However, regarding the event driven vision sensor, although such advantages described above have been known, it is hard to say that a method of using the event driven vision sensor in combination with another device has been sufficiently suggested.

In view of this, an object of the present invention is to provide an information processing device, a visual line detection system, a visual line detection method, and a visual line detection program capable of carrying out visual line detection at high speed and with high accuracy while minimizing a processing load as a result of application of the event driven vision sensor to a visual line detection technique.

Solution to Problem

According to an aspect of the present invention, there is provided an information processing device including a light source control section that changes intensity of light of a light source that irradiates eyes of a user with light, a reception section that receives, from an event driven vision sensor including a sensor that generates an event signal when detecting a change in intensity of a light to be incident thereon, the event signal indicating a position and a time of the change in intensity of the light reflected by the eyes of the user, and a visual line detection section that identifies the light source corresponding to the event signal on the basis of a relative positional relation among the eyes of the user, the light source, and the vision sensor, and of the event signal generated at the same time that control is carried out by the light source control section, to detect a visual line of the user.

According to another aspect of the present invention, there is provided a visual line detection system including a light source that irradiates eyes of a user with light, a light source control section that changes intensity of the light of the light source, an event driven vision sensor including a sensor that generates an event signal when detecting a change in intensity of a light to be incident thereon, and a terminal device including a reception section that receives the event signal indicating a position and a time of the change in intensity of the light reflected by the eyes of the user, from the vision sensor, and a visual line detection section that identifies the light source corresponding to the event signal on the basis of a relative positional relation among the eyes of the user, the light source, and the vision sensor, and of the event signal generated at the same time that control is carried out by the light source control section, to detect a visual line of the user.

According to a further aspect of the present invention, there is provided a visual line detection method including a step of changing intensity of light of a light source that irradiates eyes of a user with light, a step of receiving, from an event driven vision sensor including a sensor that generates an event signal when detecting a change in intensity of a light to be incident thereon, the event signal indicating a position and a time of the change in intensity of the light reflected by the eyes of the user, and a step of identifying the light source corresponding to the event signal on the basis of a relative positional relation among the eyes of the user, the light source, and the vision sensor, and of the event signal generated at the same time that the intensity of the light of the light source is changed, to detect a visual line of the user.

According to a still further aspect of the present invention, there is provided a visual line detection program causing a computer to realize a function of changing intensity of light of a light source that irradiates eyes of a user with light, a function of receiving, from an event driven vision sensor including a sensor that generates an event signal when detecting a change in intensity of a light to be incident thereon, the event signal indicating a position and a time of the change in intensity of the light reflected by the eyes of the user, and a function of identifying the light source corresponding to the event signal on the basis of a relative positional relation among the eyes of the user, the light source, and the vision sensor, and of the event signal generated at the same time that the intensity of the light of the light source is changed, to detect a visual line of the user.

According to the above-described configurations, it is possible to carry out visual line detection at high speed and with high accuracy while minimizing a processing load as a result of application of the event driven vision sensor to the visual line detection technique.

DESCRIPTION OF EMBODIMENTS

Hereinafter, some preferred embodiments of the present invention will be described in detail with reference to the attached drawings. Note that, in the present specification and the drawings, the same reference signs are provided to constituent elements with substantially the same functional configurations, and the description will not be repeated.

Figure 1:
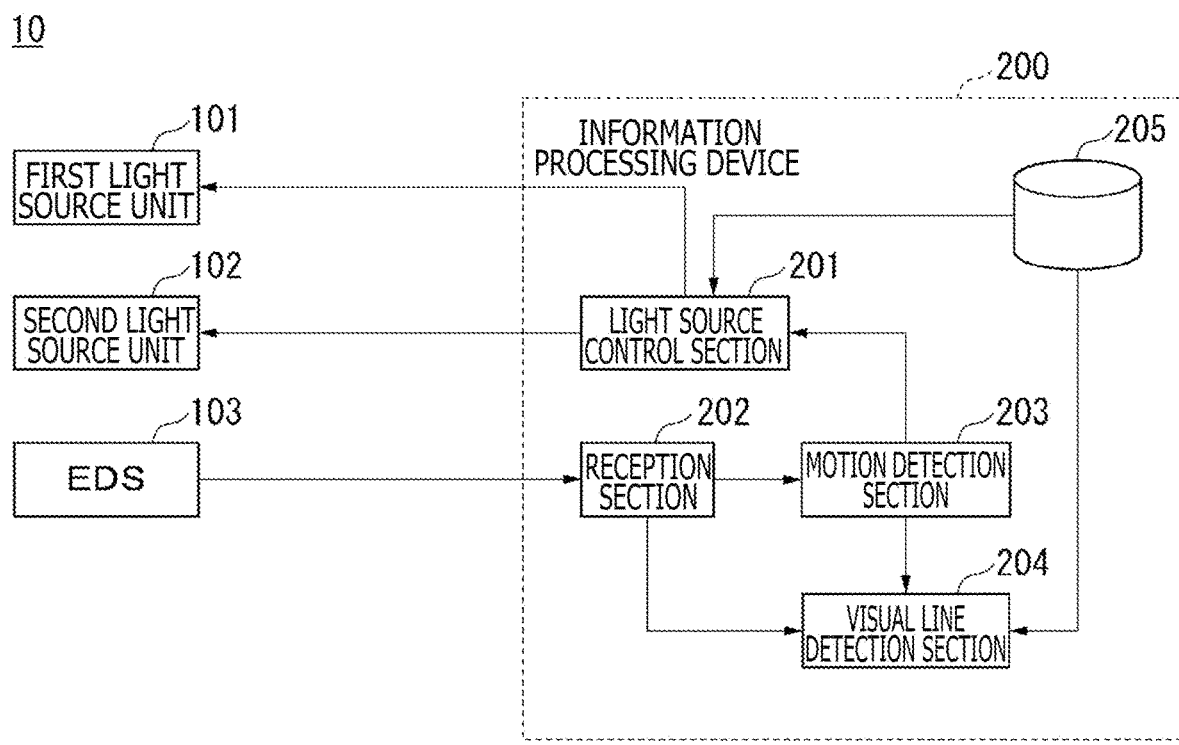
FIG. 1 is a block diagram illustrating a schematic configuration of a system according to an embodiment of the present invention.

FIG. 1 is a block diagram illustrating a schematic configuration of a visual line detection system 10 according to an embodiment of the present invention. The visual line detection system 10 according to the embodiment of the present invention may entirely be incorporated in such a device as an HMD (Head-Mounted Display) to be worn on the head of a user or may be configured such that a portion including an information processing device 200 described later is disposed at a position distant from the head of the user.

In an example illustrated in the figure, the visual line detection system 10 includes a first light source unit 101 and a second light source unit 102 each including an LED (Light Emitting Diode), an EDS (Event Driven Sensor) 103 that is an event driven vision sensor, and an information processing device 200. Among these components, the first light source unit 101, the second light source unit 102, and the EDS 103 are disposed closer to the eyes of the user, and a relative positional relation between each of the first light source unit 101, the second light source unit 102, and the EDS 103, and the eyes of the user is known.

The first light source unit 101 and the second light source unit 102 each include an LED emitting infrared light, for example, and are disposed at positions at which the infrared light can be applied to the eyes of the user. In addition, the first light source unit 101 and the second light source unit 102 are controlled by the information processing device 200. A detailed description will be given later.

The EDS 103 is an example of a vision sensor that generates an event signal when the sensor detects a change in intensity of light, and includes sensors, not illustrated, which constitute a sensor array and a processing circuit, not illustrated, which is connected to the sensors. Each of the sensors includes a light receiving element and generates an event signal when detecting a change in intensity of light to be incident thereon, more specifically, a change in luminance. In the present embodiment, the EDS 103 is disposed at a position at which a reflection image of the eyes of the user is made incident on the sensor, and generates an event signal when the sensor detects a luminance change in the reflection image of the eyes of the user. The sensor not detecting any luminance change in the reflection image of the eyes of the user does not generate an event signal. Accordingly, an event signal is generated asynchronously in time in the EDS 103. The event signal generated in the EDS 103 is output to the information processing device 200.

The event signal generated in the EDS 103 includes identification information regarding each sensor (for example, a position of a pixel), a polarity of a luminance change (higher or lower), a time stamp, and the like.

The information processing device 200 is implemented by a computer having a communication interface, a processor, and a memory, for example, and includes functions of a light source control section 201, a reception section 202, a motion detection section 203, and a visual line detection section 204 which are achieved by the processor being operated according to a program stored in the memory or received through the communication interface. In addition, the information processing device 200 includes an irradiation pattern memory 205 that stores an irradiation pattern for controlling each of the first light source unit 101 and the second light source unit 102. The irradiation pattern memory 205 is referenced by the light source control section 201 and the visual line detection section 204. The functions of the individual sections will be described in more detail below.

When receiving a trigger to be described later from the motion detection section 203, the light source control section 201 transmits a control signal to each of the first light source unit 101 and the second light source unit 102 according to a corresponding irradiation pattern stored in the irradiation pattern memory 205.

Specifically, the light source control section 201 carries out control of turn-on or turn-off of each light source or control of intensity of light irradiated from each light source. At this time, the light source control section 201 controls the first light source unit 101 and the second light source unit 102 independently of each other, according to different irradiation patterns.

The reception section 202 receives an event signal generated in the EDS 103. Here, the event signal received by the reception section 202 is one generated when the EDS 103 detects a luminance change in the reflection image of the eyes of the user. In particular, in a case in which the first light source unit 101 and the second light source unit 102 are controlled by the light source control section 201 described above, a luminance change occurs in the reflection image of the eyes of the user, according to control by the light source control section 201. Due to the luminance change, the event signal is generated and received by the reception section 202. For example, in a case in which the first light source unit 101 is lit by the light source control section 201, an event signal indicating a position corresponding to the first light source unit 101 and a polarity corresponding to turn-on is received by the reception section 202. Meanwhile, for example, in a case in which the second light source unit 102 is turned off by the light source control section 201, an event signal indicating a position corresponding to the second light source unit 102 and a polarity corresponding to turn-off is received by the reception section 202.

Figure 2:
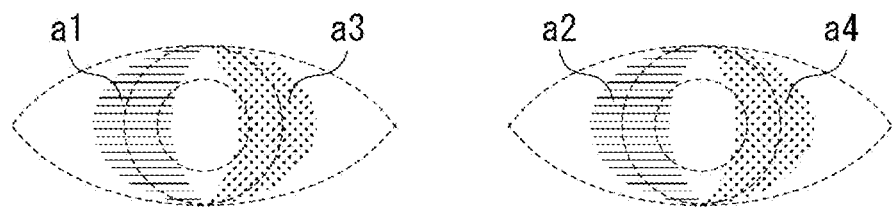
FIG. 2 is a diagram for schematically explaining motion detection according to the embodiment of the present invention.

The motion detection section 203 detects presence or absence of a motion of a visual line of the user on the basis of the event signal received by the reception section 202. FIG. 2 is a schematic diagram illustrating an event signal generated in a case in which the visual line of the user is moved in a horizontal direction. Regions a1 and a2 in FIG. 2 indicate that a polarity of the luminance change is a first direction (either of + or −), while regions a3 and a4 indicate that a polarity of the luminance change is a second direction opposite to the first direction (an opposite direction to the first direction, of + or −). As illustrated in FIG. 2, when the visual line of the user moves in the horizontal direction, an event signal indicating the same polarity on the same side as viewed from the EDS 103 is generated in each of the right and left eyes. Also, in each of the right and left eyes, an event signal indicating that a polarity on the inner corner side with respect to the eye is opposite to a polarity on the corner side with respect to the eye.

In this manner, the event signal generated in response to the motion of the visual line of the user has characteristics in a position and a polarity. The motion detection section 203 collates patterns prepared in advance so as to correspond to such characteristics with the event signal received by the reception section 202, and accordingly, the motion detection section 203 detects presence or absence of the motion of the visual line of the user or an appropriate orientation thereof. Note that, although the event signal is generated also in a case in which the user blinks, the motion detection section 203 uses the patterns described above so as to be able to distinguish the motion of the visual line of the user and the blink from each other.

Note that, although a detailed description will be described later, at a time point at which the detection by the motion detection section 203 described above is carried out, the first light source unit 101 and the second light source unit 102 may be turned off. However, even when light is not irradiated on the eyes of the user by the first light source unit 101 and the second light source unit 102, the EDS 103 generates the event signal in response to the motion of the visual line of the user, so that the motion detection section 203 can detect presence or absence of the motion of the visual line of the user, irrespective of turn-on or turn-off of the first light source unit 101 and the second light source unit 102.

Then, when detecting the motion of the visual line of the user as described above, the motion detection section 203 transmits a trigger causing control of any of the first light source unit 101 and the second light source unit 102 to be started, to the light source control section 201. Control that is started by the light source control section 201 due to this trigger is for carrying out detection of the visual line of the user more accurately, and in the present embodiment, the light source control section 201 turns each of the first light source unit 101 and the second light source unit 102 on or off according to each corresponding irradiation pattern stored in the irradiation pattern memory 205.

In addition, the motion detection section 203 supplies information indicating a result of the motion detection to the visual line detection section 204.

The visual line detection section 204 detects the visual line of the user on the basis of the event signal received by the reception section 202.

Figure 3:
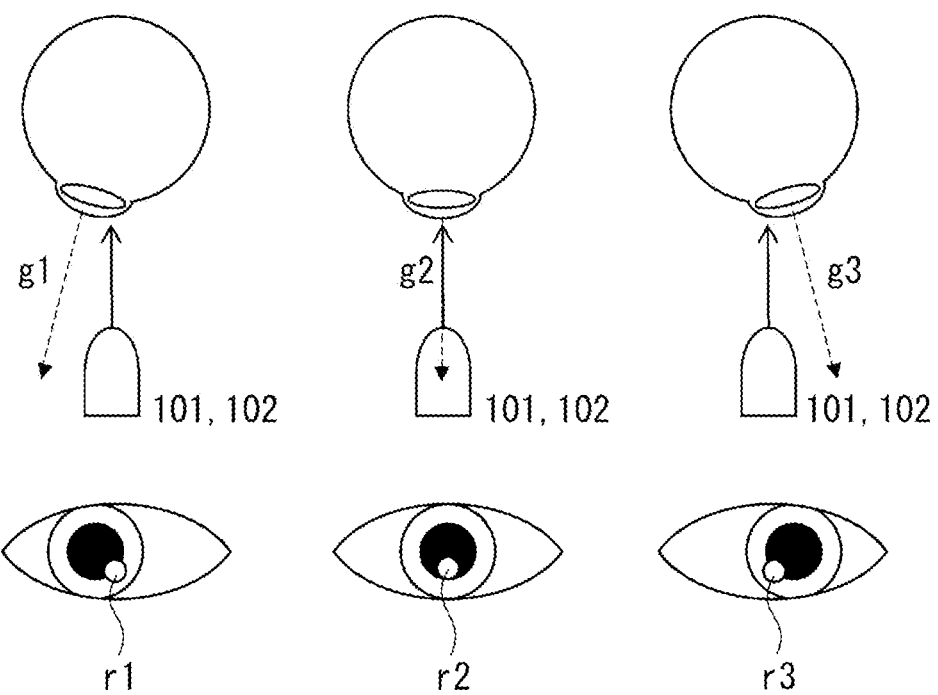
FIG. 3 is a diagram for schematically explaining visual line detection according to the embodiment of the present invention.

Here, the reflection images of the first light source unit 101 and the second light source unit 102 will be described with reference to FIG. 3. Upper parts in FIG. 3 illustrate relations between the first light source unit 101 and the second light source unit 102 and the visual line of the user, while lower parts in FIG. 3 illustrate positions of the reflection images in the event signals generated in the respective states corresponding to the upper parts. In addition, the figure on the left side in FIG. 3 indicates a case in which the visual line of the user is directed in a direction of an arrow g1, the figure on the central side in FIG. 3 indicates a case in which the visual line of the user is directed in a direction of an arrow g2, and the figure on the right side in FIG. 3 indicates a case in which the visual line of the user is directed in a direction of an arrow g3. As illustrated in FIG. 3, according to the orientation of the visual line of the user, the positions of reflection images r1, r2, and r3 of the light sources change.

As described above, in the visual line detection system 10, since a relative positional relation between each of the first light source unit 101, the second light source unit 102, and the EDS 103, and the eyes of the user is known, the visual line detection section 204 identify a relative position between pupils of the user and each of the reflection images r1, r2, and r3 of the light sources, on the basis of the event signal received by the reception section 202 and carries out geometric calculation, thereby detecting a direction of the visual line of the user. Note that a method of identifying the reflection image of light irradiated from the first light source unit 101 and the reflection image of light irradiated from the second light source unit 102 in the event signal will be described later.

Figure 4:
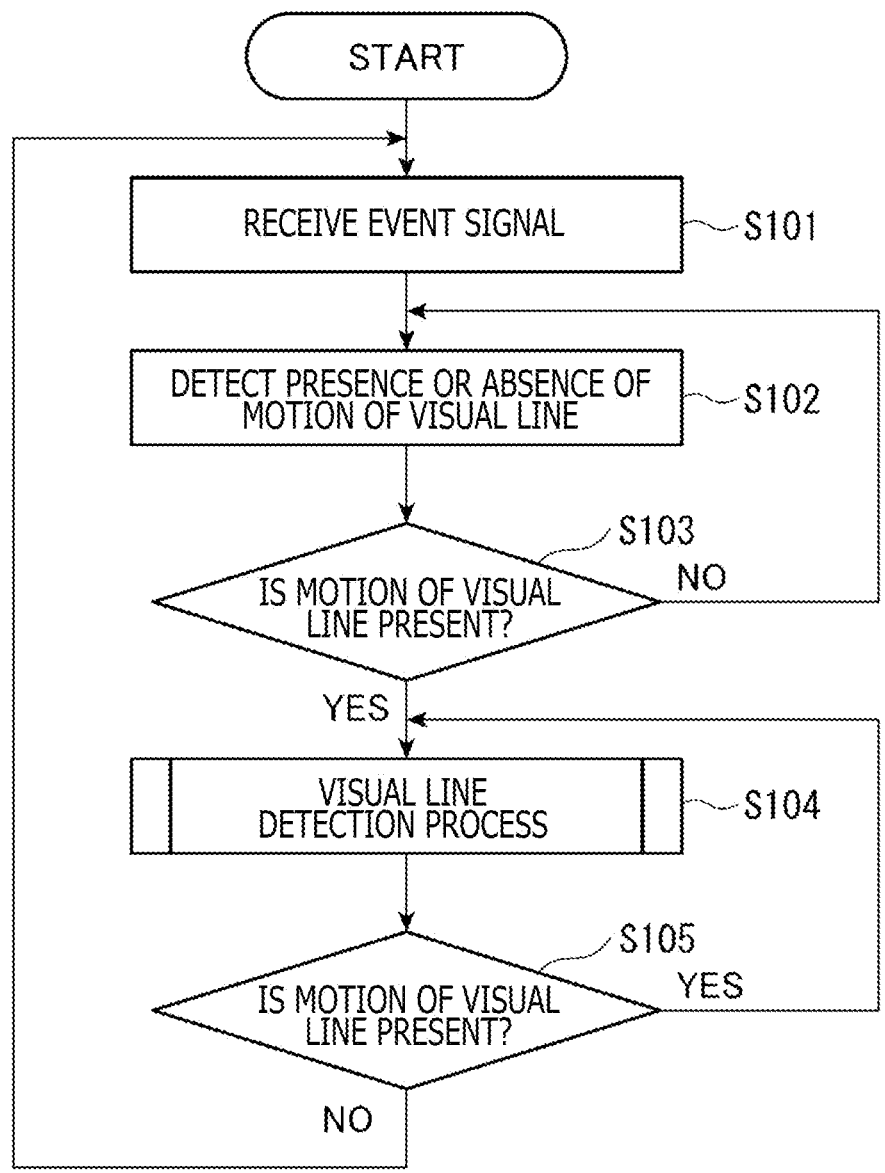
FIG. 4 is a flow chart indicating an example of a processing method according to the embodiment of the present invention.

FIG. 4 is a flow chart indicating an example of a visual line detecting method of the user according to the embodiment of the present invention. In the example illustrated in the figure, the reception section 202 of the information processing device 200 receives an event signal generated by the EDS 103 (step S101), and the motion detection section 203 detects presence or absence of a motion of the visual line of the user on the basis of the event signal (step S102). The motion detection section 203 determines whether or not the motion of the visual line of the user is present (step S103), and in a case in which the motion of the visual line of the user is present, the visual line detection section 204 carries out a visual line detection process to be described later (step S104). Even after the visual line detection process is started, the motion detection section 203 detects presence or absence of the motion of the visual line of the user (step S105), and during presence of the motion of the visual line of the user, the visual line detection section 204 repeats the visual line detection process. In contrast, in a case in which the motion of the visual line of the user is absent, the visual line detection process is not carried out until next determination that the motion of the visual line of the user is present is made on the basis of the event signal (steps S101 to S103).

Figure 5:
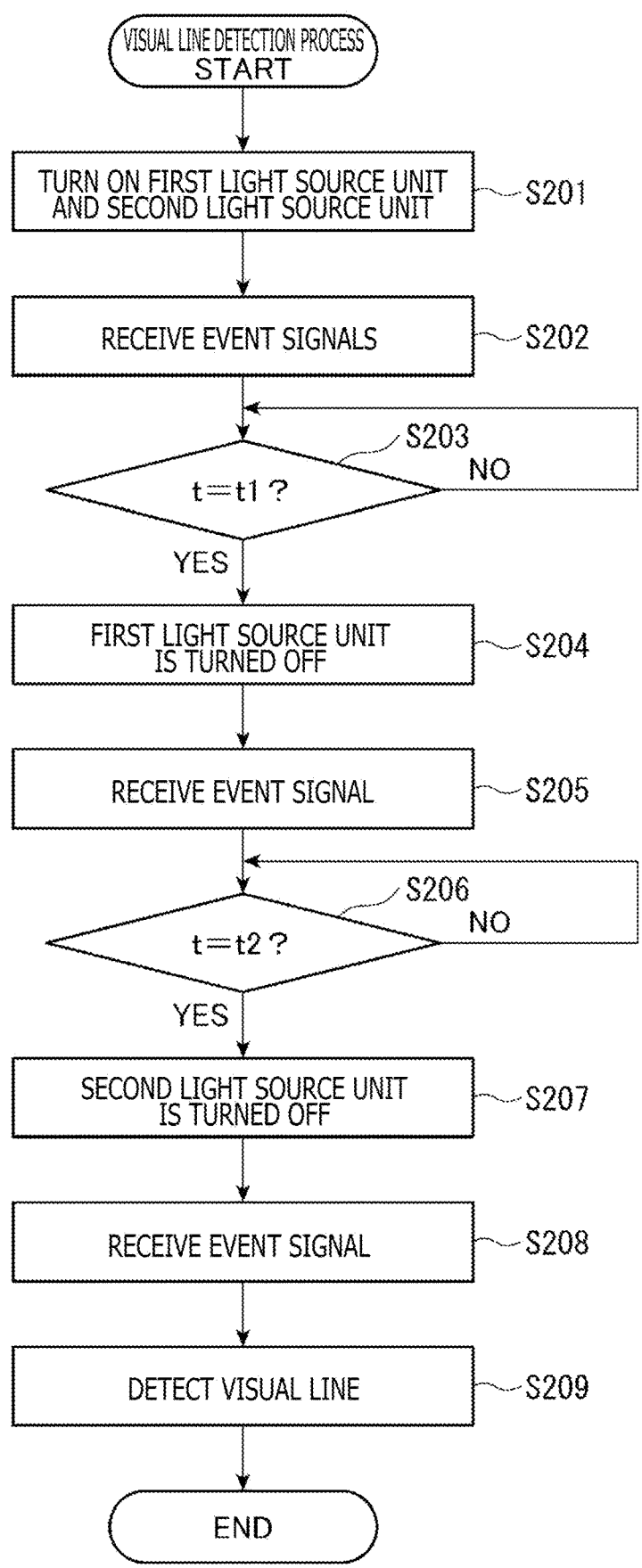
FIG. 5 is a (detailed) flow chart indicating an example of a processing method according to the embodiment of the present invention.
Figure 6:
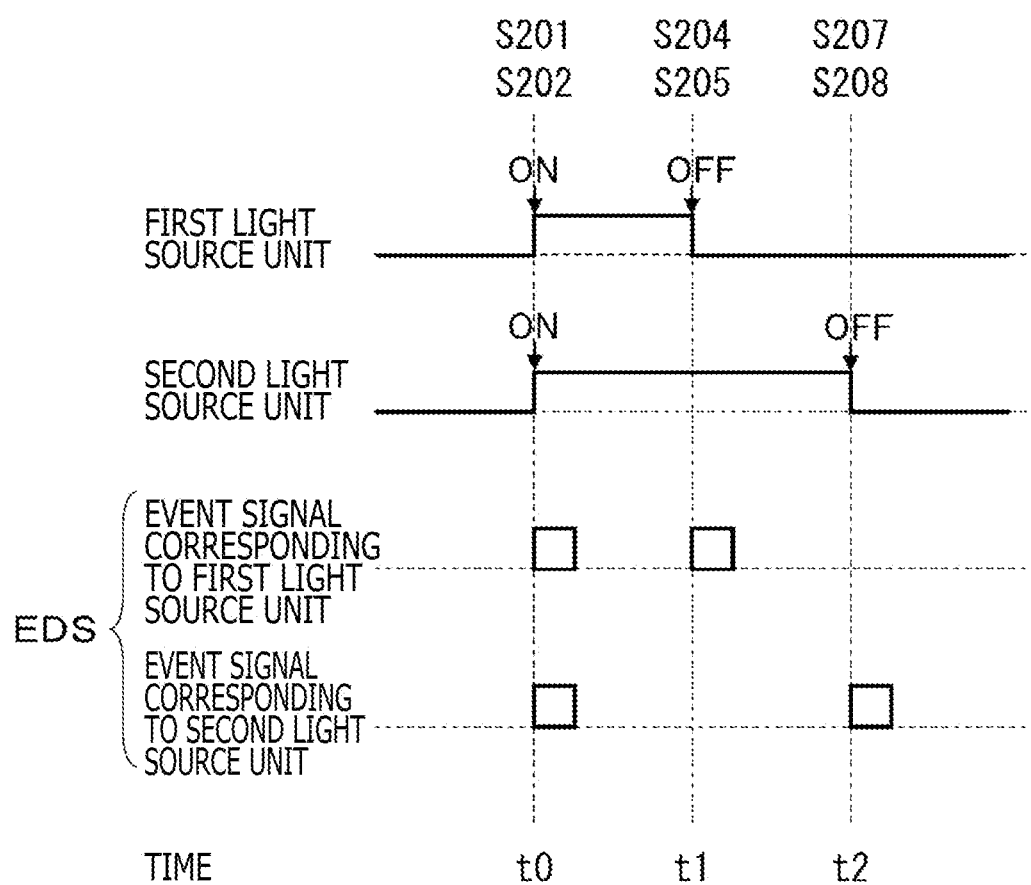
FIG. 6 is a diagram for schematically explaining light source control according to the embodiment of the present invention.

FIG. 5 is a flow chart indicating details of the visual line detection process in FIG. 4, and FIG. 6 is a diagram for explaining light source control at a time of carrying out the flow chart to be explained in FIG. 5. In the example illustrated in the figure, the light source control section 201 of the information processing device 200 transmits a control signal to turn on the first light source unit 101 and the second light source unit 102 at the same time (step S201). At this time, the reception section 202 receives event signals generated by the EDS 103 (step S202). The event signals received by the reception section 202 in step S202 are event signals generated in response to a change in intensity of light which occurs as a result of turning-on of the first light source unit 101 and the second light source unit 102 in step S201.

Here, the event signals generated by the EDS 103 are generated asynchronously in time and at high speed, different from the conventional frame-based vision sensor, for example, and accordingly, in a case in which the first light source unit 101 and the second light source unit 102 are turned on almost at the same time, the event signals each indicating turning-on of each of the first light source unit 101 and the second light source unit 102 are generated almost at the same time in the EDS 103 as well. Thus, in FIG. 6, a time at which the light source control section 201 turns on the first light source unit 101 and the second light source unit 102 in step S201, and a time (time stamp) at which the event signals are received in step S202 are each set to a time t0.

Next, the motion detection section 203 determines whether or not a predetermined period of time has passed since the first light source unit 101 and the second light source unit 102 were turned on at the same time and a time becomes t1 (step S203). Then, in a case in which the time becomes t1, the light source control section 201 transmits a control signal to turn off the first light source unit 101 (step S204). At this time, the reception section 202 receives the event signal generated by the EDS 103 (step S205). The event signal received by the reception section 202 in step S205 is an event signal generated in response to a change in intensity of light which occurs as a result of turning-off of the first light source unit 101 in step S204.

Here, in FIG. 6, similarly to the relation between step S201 and step S202 described above, a time at which the light source control section 201 turns off the first light source unit 101 in step S204 and a time (time stamp) at which the event signal is received in step S205 are each set to t1.

Next, the motion detection section 203 determines whether or not a predetermined period of time has passed since the first light source unit 101 was turned off and a time becomes t2 (step S206). Then, in a case in which the time becomes t2, the light source control section 201 transmits a control signal to turn off the second light source unit 102 (step S207). At this time, the reception section 202 receives an event signal generated by the EDS 103 (step S208). The event signal received by the reception section 202 in step S208 is an event signal generated in response to a change in intensity of light which occurs as a result of turning-off of the second light source unit 102 in step S207.

Here, in FIG. 6, similarly to the relation between step S201 and step S202 and the relation between step S204 and step S205 described above, a time at which the light source control section 201 turns off the second light source unit 102 in step S207 and a time (time stamp) at which the event signal is received in step S208 are each set to t2.

Lastly, the visual line detection section 204 detects the visual line of the user on the basis of the event signals received by the reception section 202 in steps S202, S205, and S208 (step S209).

Here, according to information provided in advance and the event signals received by the reception section 202 in steps S202, S205, and S208, the following information is identified at a time point in step S209.

a relative positional relation between each of the first light source unit 101 and the second light source unit 102 and the eyes of the user
  a state of turning-off or turning-on of the first light source unit 101 and the second light source unit 102 in a time series
  a relative positional relation between the EDS 103 and the eyes of the user
  a position where each event occurs in time series
  a polarity of a luminance change
  a time stamp For example, at the time t0 in FIG. 6, the first light source unit 101 and the second light source unit 102 are turned on at the same time, and accordingly, the events having the same polarity of a luminance change occur at respective positions corresponding to the first light source unit 101 and the second light source unit 102. Accordingly, at the time t0, the event signals indicating the events that occur as a result of turning-on of the first light source unit 101 and the second light source unit 102 are generated.

Next, at the time t1 in FIG. 6, the first light source unit 101 only is turned off, and accordingly, an event a polarity of a luminance change of which is a direction opposite to the time t0 occurs only at a position corresponding to the first light source unit 101. Note that the second light source unit 102 keeps being turned on at the time t1 and a luminance change does not occur, and as a result, an event does not occur at a position corresponding to the second light source unit 102. Thus, at the time t1, the event signal indicating only the event having occurred as a result of turning-off of the first light source unit 101 is generated.

Then, at the time t2 in FIG. 6, the second light source unit 102 is turned off, and accordingly, an event a polarity of a luminance change is a direction opposite to the time t0 and same as the time t1 occurs only at a position corresponding to the second light source unit 102. Note that the first light source unit 101 keeps being turned off at the time t2 and a luminance change does not occur, and as a result, an event does not occur at a position corresponding to the first light source unit 101. Thus, at the time t2, the event signal indicating only the event having occurred as a result of turning-off of the second light source unit 102 is generated.

In this manner, since the event signal is generated by the EDS 103 at the same time that control by the light source control section 201 is carried out, it is possible to identify that each generated event signal is based on a luminance change in the reflection image of light irradiated from which one of the light sources.

Accordingly, at a time point in step S209, due to turning-on or turning-off of each light source, the visual line detection section 204 can easily grasp what kind of polarity an event has and where the event has occurred at each time. Hence, the visual line detection section 204 can carry out detection of the visual line of the user on the basis of the event signal generated at a timing at which each of the first light source unit 101 and the second light source unit 102 is turned off or on, without complicated calculation. It is possible to detect the visual line of the user by using a position of reflected light of each of the first light source unit 101 and the second light source unit 102, through a pupil corneal reflection method, for example. When detecting the visual line, the visual line detection section 204 may use a detection result of presence or absence of a motion of the visual line of the user carried out in step S102 in FIG. 4. For example, the visual line detection section 204 may limit a range of the visual line detection carried out in step S209 in FIG. 5, on the basis of the detection result in step S102.

Here, as illustrated in FIGS. 5 and 6, at a time point at which the visual line detection process described is ended, the first light source unit 101 and the second light source unit 102 are turned off. In other words, when the detection process of the visual line of the user is started, the first light source unit 101 and the second light source unit 102 are turned on, and at a time point at which the visual line detection process is ended, the first light source unit 101 and the second light source unit 102 are turned off. Accordingly, turning-on of the first light source unit 101 and the second light source unit 102 is limited to a necessary timing, so that power consumption can be expected to be reduced.

Note that, in the example illustrated in FIG. 4, an example in which the visual line detection process illustrated in FIGS. 5 and 6 is carried out in a case in which a motion of the visual line of the user is detected. Alternatively, there may be adopted a configuration in which the visual line detection process illustrated in FIGS. 5 and 6 is constantly carried out. In addition, in the example illustrated in FIGS. 5 and 6, the example in which the first light source unit 101 and the second light source unit 102 are turned off at a different timing after being turned on at the same timing. However, the present invention is not limited to this example. For example, each of the light source units may be turned on at a different timing.

In the embodiment of the present invention described above, there are provided the light source control section 201 that causes intensity of light of each of the first light source unit 101 and the second light source unit 102 which each irradiate light on the eyes of the user to be changed, and the EDS 103 that generates an event signal indicating a position of a change in intensity of light reflected on the eyes of the user and a time thereof. Then, on the basis of a relative positional relation among the eyes of the user, the first light source unit 101, the second light source unit 102, and the EDS 103, and of an event signal generated at the same time that control by the light source control section 201 is carried out, a light source corresponding to the event signal is identified, and the visual line of the user is detected. Hence, it is possible to accurately identify a correlation between the control of the first light source unit 101 and the second light source unit 102 and generation of the event signal by the EDS 103 by use of time information regarding control of any of the light sources by the light source control section 201 and time information regarding generation of the event signal by the EDS 103. Accordingly, it is possible to carry out visual line detection at high speed and with high accuracy, while minimizing a processing load.

Note that, although the visual line detection process is often required to be performed in real time, according to the embodiment of the present invention, since an event signal due to control of a light source is generated by the EDS 103 almost at the same time that the light source control section 201 controls the light source, accuracy of time information is high. Hence, it is possible to reduce a processing load relating to control and calculation, and a real-time and highly accurate process can be carried out. In addition, since the EDS 103 is a vision sensor that generates an event signal only when the sensor detects intensity of light, it is possible to minimize power consumption, compared with a case in which constant imaging is carried out by use of an image sensor. Moreover, since a correlation between control of the first light source unit 101 and the second light source unit 102 and generation of an event signal by the EDS 103 is accurately identified, the EDS 103 is less likely to be affected by external light even outdoors, for example.

In addition, in the embodiment of the present invention, when the motion detection section 203 detects presence or absence of a motion of a visual line of a user according to an event signal and detects the motion of the visual line of the user, control of any of the light sources by the light source control section 201 is started. Accordingly, the visual detection process is carried out only in a case in which there is a possibility that the visual line of the user may be moved, so that it is possible to avoid unnecessary light source control and an unnecessary visual line detection process and reduce more power consumption, while keeping necessary accuracy.

In addition, in the embodiment of the present invention, the light source control section 201 controls intensity of light of each of the first light source unit 101 and the second light source unit 102 independently of each other, and the visual line detection section 204 identifies, in each event signal, a position at which an event occurs due to an intensity change of light of the first light source unit 101 as a position of reflection light of the first light source unit 101 and identifies a position at which an event occurs due to an intensity change of light of the second light source unit 102 as a position of reflection light of the second light source unit 102. Thus, the first light source unit 101 and the second light source unit 102 are turned on or off at timings different from each other, so that, when an event signal generated by the EDS 103 is obtained at the same time that control of any of the light sources is carried out by the light source control section 201, the light source corresponding to the event signal can be easily identified.

Note that the visual line detection system 10 which has been described in the foregoing examples may be implemented in a single device or may also be distributed and implemented in a plurality of devices. For example, the whole visual line detection system 10 may be implemented in a terminal device including an HMD, or the information processing device 200 may be separated to be implemented in a server device. In addition, assuming a use for data analysis for the purpose of marketing or the like, there may be adopted such a configuration that an irradiation pattern of a light source and an event signal are associated with each other in time series and stored as data to carry out the visual line detection process after that. In this case, the visual line detection process may also be configured to be carried out by another device such as the light source control section, the reception section, and the motion detection section.

In addition, in the visual line detection system 10 that has been described in the foregoing examples, an example in which the visual line detection system 10 includes two light source (the first light source unit 101 and the second light source unit 102) is provided. However, as long as a relative positional relation between each light source and the eyes of the user is identified, the number of light source included in the visual line detection system 10 may be one or three or more. Particularly in a configuration in which three light sources are included, some or all of the light sources are turned on or off at timings different from one another, so that detailed information such as three-dimensional information can be expected to be obtained.

Moreover, in the visual line detection system 10 that has been described in the foregoing examples, an example in which two light sources (the first light source unit 101 and the second light source unit 102) are turned on or off in the visual line detection process is provided. However, there may be adopted such a configuration that each light source is not turned off completely and intensity of light to be irradiated from each light source is changed.

Moreover, in the visual line detection system 10 that has been described in the foregoing examples, an example in which the visual line detection system 10 includes one vision sensor (EDS 103) is provided. However, as long as a relative positional relation between each vision sensor and the eyes of the user is identified, the visual line detection system 10 may include a plurality of vision sensors. Particularly in a configuration in which a plurality of vision sensors are included, arrangement of each vision sensor, control of the light source, and the like are contrived, so that more detailed information such as three-dimensional information can be expected to be obtained.

While some embodiments of the present invention have been described above in detail with reference to the attached drawings, the present invention is not limited to the examples. It is apparent that those with normal knowledge in the technical field of the present disclosure can make various changes or modifications within the scope of the technical idea described in the claims, and it is understood that the changes and the modifications obviously belong to the technical scope of the present invention.

REFERENCE SIGNS LIST

10: Visual line detection system
101: First light source unit
102: Second light source unit
103: EDS 200: Information processing device
201: Light source control section
202: Reception section
203: Motion detection section
204: Visual line detection section
205: Irradiation pattern memory

The invention claimed is:

1. An information processing device, comprising:
circuitry configured to
change an intensity of light of a light source that irradiates first and second eyes of a user with light;
receive, from an event driven vision sensor including a sensor that generates an event signal when detecting a change in intensity of a light to be incident thereon, the event signal indicating a position and a time of the change in intensity of the light reflected in first and second regions of the first eye and in third and fourth regions of the second eye of the user;
identify the light source corresponding to the event signal based on the event signal and positions of the eyes of the user, the light source, and the vision sensor; and
detect a visual line of the user according to the identified light source, wherein
the first and second regions are adjacent to a pupil of the first eye and the third and fourth regions are adjacent to a pupil of the second eye,
the first region is at an outer corner side of the pupil of the first eye,
the second region is at an inner corner side of the pupil of the first eye,
the third region is at an inner corner side of the pupil of the second eye, and
the fourth region is at an outer corner side of the pupil of the second eye.

2. The information processing device according to claim 1, wherein the circuitry is further configured to:
detect presence or absence of a motion of the visual line of the user, from the event signal; and
control of the light source when a motion of the visual line of the user is detected.

3. The information processing device according to claim 1, wherein the circuitry is further configured to
control the intensity of light of each of a plurality of the light sources, independently of each other, the plurality of the light sources including at least a first light source and a second light source, and
identify, in the event signal, a position at which an event occurs due to the change in the intensity of light of the first light source, as a position of reflection light of the first light source, and identify a position at which an event occurs due to the change in the intensity of light of the second light source, as a position of reflection light of the second light source.

4. A visual line detection system, comprising:
a light source that irradiates first and second eyes of a user with light;
an event driven vision sensor including a sensor that generates an event signal when detecting a change in intensity of a light to be incident thereon; and
information processing device including circuitry configured to
change an intensity of light of the light source;
receive, from the event driven vision sensor, the event signal indicating a position and a time of the change in intensity of the light reflected in first and second regions of the first eye and in third and fourth regions of the second eye of the user; and
identify the light source corresponding to the event signal based on the event signal and positions of the eyes of the user, the light source, and the vision sensor; and
detect a visual line of the user according to the identified light source, wherein
the first and second regions are adjacent to a pupil of the first eye and the third and fourth regions are adjacent to a pupil of the second eye,
the first region is at an outer corner side of the pupil of the first eye,
the second region is at an inner corner side of the pupil of the first eye,
the third region is at an inner corner side of the pupil of the second eye, and
the fourth region is at an outer corner side of the pupil of the second eye.

5. A visual line detection method, comprising:
changing an intensity of light of a light source that irradiates first and second eyes of a user with light;
receiving, from an event driven vision sensor including a sensor that generates an event signal when detecting a change in intensity of a light to be incident thereon, the event signal indicating a position and a time of the change in intensity of the light reflected in first and second regions of the first eye and in third and fourth regions of the second eye of the user;
identifying the light source corresponding to the event signal based on the event signal and positions of the eyes of the user, the light source, and the vision sensor; and
detecting a visual line of the user according to the identified light source, wherein
the first and second regions are adjacent to a pupil of the first eye and the third and fourth regions are adjacent to a pupil of the second eye,
the first region is at an outer corner side of the pupil of the first eye,
the second region is at an inner corner side of the pupil of the first eye,
the third region is at an inner corner side of the pupil of the second eye, and
the fourth region is at an outer corner side of the pupil of the second eye.

6. A non-transitory computer readable medium storing computer executable instructions which, when executed by a computer, cause the computer to:
change intensity of light of a light source that irradiates first and second eyes of a user with light;
receive, from an event driven vision sensor including a sensor that generates an event signal when detecting a change in intensity of a light to be incident thereon, the event signal indicating a position and a time of the change in intensity of the light reflected in first and second regions of the first eye and in third and fourth regions of the second eye of the user; and
identify the light source corresponding to the event signal on a basis of a relative positional relation among the eyes of the user, the light source, and the vision sensor, and of the event signal generated at a same time that the intensity of the light of the light source is changed, to detect a visual line of the user, wherein
the first and second regions are adjacent to a pupil of the first eye and the third and fourth regions are adjacent to a pupil of the second eye, the first region is at an outer corner side of the pupil of the first eye, the second region is at an inner corner side of the pupil of the first eye, the third region is at an inner corner side of the pupil of the second eye, and the fourth region is at an outer corner side of the pupil of the second eye.

7. The information processing device according to claim 1, wherein the event signal indicates a positive polarity of the change in intensity based on the first and third regions, and the circuitry detects the visual line to have moved in a first direction according to the positive polarity indicated in the event signal.

8. The information processing device according to claim 7, wherein the event signal indicates a negative polarity of the change in intensity based on the second and fourth regions, and the circuitry detects the visual line to have moved in a second direction opposite the first direction according to the negative polarity indicated in the event signal.

9. The information processing device according to claim 7, wherein the first direction is a horizontal direction.

10. The information processing device according to claim 7, wherein the first direction is a vertical direction.

* * * * *